US006967237B2

(12) United States Patent
Bednarek

(10) Patent No.: US 6,967,237 B2
(45) Date of Patent: Nov. 22, 2005

(54) GHRELIN ANALOGS

(75) Inventor: Maria A. Bednarek, Colonia, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/276,392

(22) PCT Filed: May 25, 2001

(86) PCT No.: PCT/US01/17026

§ 371 (c)(1),
(2), (4) Date: Nov. 15, 2002

(87) PCT Pub. No.: WO01/92292

PCT Pub. Date: Dec. 6, 2001

(65) Prior Publication Data

US 2003/0186844 A1 Oct. 2, 2003

Related U.S. Application Data

(60) Provisional application No. 60/207,920, filed on May 30, 2000.

(51) Int. Cl.$^7$ ......................... A61K 38/00; C07K 14/00; C07K 16/00; C07K 2/00; C07K 4/00
(52) U.S. Cl. ........................ 530/300; 530/327; 530/328
(58) Field of Search ................................. 530/350, 328, 530/329, 330, 327, 326, 300; 514/12, 16, 18

(56) References Cited

FOREIGN PATENT DOCUMENTS

| EP | 1 197 496 | | 4/2002 |
|---|---|---|---|
| JP | 2000WO-JP04907 | * | 2/2000 |
| WO | WO98/42840 | | 10/1998 |
| WO | WO99/63088 | | 12/1999 |
| WO | WO01/07475 | | 2/2001 |

OTHER PUBLICATIONS

Kojima et al., Ghrelin is growth–hormone–releasing acylated peptide from stomach, Dec. 9, 1999, Nature, vol. 402, pp. 656–660.*
Dieguez, C. et al. "Ghrelin: a step forward in the understanding of somatotroph cell function and growth regulation", European Journal of Endocrinology, 2000, vol. 142, pp. 413–417.
Bednarek, M. et al. "Structure–Function Studies on the New Growth Hormone–Releasing Peptide, Ghrelin: Minimal Sequence of Ghrelin Necessary for Activation of Growth Hormone Secretagogue Receptor 1 a", Journal of Medicinal Chemistry, 2000, vol. 43, pp. 4370–4376.
Bluet–Pajot, M–T. et al. "Hypothalamic and Hypophyscal Regulation of Growth Horomone Secreation", Cellular and Molecular Neurobiology, 1998, vol. 18, pp. 101–104.
Hosoda, H. et al. "Purification and Characterization of Rat des–Gln14–Ghrelin, a Second Endogenous Ligand for the Growth Hormone Secretagogue Receptor", The Journal of Biological Chemistry, 2000, vol. 275, pp. 21995–22000.

Bowers, C. "Novel GH–Releasing Peptides", Endocrine Research and Education, Inc., Los Angeles, CA in Molecular and Clinical Advances in Pituitary Disorders, 1993, Chapter 23, pp. 153–157.
Bowers, C. et al., "On the in Vitro and in Vivo Activity of a New Synthetic Hexapeptide that Acts on the Pituitary to Specifically Release Growth Hormone", Endocrinology, 1984, vol. 114, pp. 1537–1545.
Chen, C. "Growth Hormone Secretagogue Actions on the Pituitary Gland: Multiple Receptors for Multiple Ligands?", Clinical and Experimental Pharmacology and Physiology, 2000, vol. 27, pp. 323–329.
Chen, M. et al., "Analogs of the Orally Active Growth Hormone Secretagogue L–162,752", Bioorganic & Medicinal Chemistry Letters, 1996, vol. 6, pp. 2163–2168.
Cheng, K. et al., "The Synergistic Effects of His–D–Trp–Ala–Trp–D–Phe–Lys–NH2 on growth Hormone (GH)–Releasing Factor–Stimulated GH Release and Intracellular Adenosine 3',5'–Monophosphate Accumulation in Rat Primary Pituitary Cell Culture", Endocrinology, 1989, vol. 124, pp. 2791–2798.
Deghenghi, R. et al., "GH–Releasing Activity of Hexarelin, A New Growth Hormone Releasing Peptide, in Infant and Adult Rats", Life Sciences, 1994, vol. 54, pp. 1321–1328.
Frohman, L. et al., "Growth Hormone–Releasing Hormone", Endocrine Reviews, 1986, vol. 7, pp. 223–253.
Guan, X. et al., "Distribution of mRNA encoding the growth hormone secretagogue receptor in brain and peripheral tissues", Molecular Brain Research, 1997, vol. 48, pp. 23–29.
Howard, A. et al., "A Receptor in Pituitary and Hypothalamus That Functions in Growth Hormone Release", Science, 1996, vol. 273, pp. 974–977.
Kineman, R. et al., "Growth Hormone (GH)–Releasing Hormone (GHRH) and the GH Secretagogue (GHS), L692, 585, Differentially Modulate Rat Pituitary GHS Receptor and GHRH Receptor Messenger Ribonuleic Acid Levels", Endocrinology, 1999, vol. 140, pp. 3581–3586.
Kojima, M. et al., "Ghrelin is a growth–hormone–releasing acylated peptide from stomach", Nature, 1999, vol. 402, pp. 656–660.
Kojima, M. et al., "Ghrelin is a novel growth hormone releasing acylated peptide from stomach", Third International Symposium on Growth Hormone Secretagogues, Keystone, Colorado, Feb. 17–19, 2000.

(Continued)

Primary Examiner—Jon Weber
Assistant Examiner—Robert B. Mondesi
(74) Attorney, Agent, or Firm—Sheldon O. Heber; Jack L. Tribble

(57) ABSTRACT

The present invention features truncated ghrelin analogs active at the GHS receptor. Ghrelin is a naturally occurring modified peptide. The analogs can bind to the GHS receptor and, preferably, bring about signal transduction. Ghrelin analogs have a variety of different uses including being used as a research tool and being used therapeutically.

14 Claims, No Drawings

OTHER PUBLICATIONS

Kulju McKee, K. et al., "Cloning and Characterization of Two Human G Protein–Coupled Receptor Genes (GPR38 and GPR39) Related to the Growth Hormone Secretagogue and Neurotensin Receptors", Genomics, 1997, vol. 46, pp. 426–434.

Patchett, A. et al., "Design and biological activities of L–163,191 (MK–0677): A potent, orally growth hormone secretagogue", Proc. Natl. Acad. Sci. USA, 1995, vol. 92, pp. 7001–7005.

Pong, S. et al., "Identification of a New G–Protein–Linked Receptor for Growth Hormone Secretagogues", Molecular Endocrinology, 1996, vol. 10, pp. 57–61.

Smith, R. et al., "A Nonpeptidyl Growth Hormone Secretagogue", Science, 1993, vol. 260, pp. 1640–1643.

Strobl, J. et al., "Human Growth Hormone", Pharmacological Reviews, 1994, vol. 46, pp. 1–34.

* cited by examiner

GHRELIN ANALOGS

CROSS-REFERENCE TO RELATED APPLICATIONS

The present application claims priority to provisional application U.S. Ser. No. 60/207,920, filed May 30, 2000, hereby incorporated by reference herein.

BACKGROUND OF THE INVENTION

The references cited herein are not admitted to be prior art to the claimed invention.

The pulsatile release of growth hormone from the pituitary somatotrops is regulated by two hypothalamic neuropeptides: growth hormone-releasing hormone and somatostatin. Growth hormone-releasing hormone stimulates release of growth hormone, whereas, somatostatin inhibits secretion of growth hormone. (Frohman et al., *Endocronol. Rev.* 1986, 7, 223–253, and Strobl et al., *Pharmacol. Rev.* 1994, 46, 1–34.)

Release of growth hormone from the pituitary somatotrops can also be controlled by growth hormone-releasing peptides. A hexapeptide His-D-Trp-Ala-Trp-D-Phe-Lys-amide (GHRP-6), was found to release growth hormone from somatotrops in a dose-dependent manner in several species including man. (Bowers et al., *Endocrinology* 1984, 114, 1537–1545.) Subsequent chemical studies on GHRP-6 led to the identification of other potent growth-hormone secretagogues such as GHRP-1, GHRP-2 and hexarelin (Cheng et al., *Endocrinology* 1989, 124, 2791–2798, Bowers, C. Y. Novel GH-Releasing Peptides. In: *Molecular and Clinical Advances in Pituitary Disorders*. Ed: Melmed, S.; Endocrine Research and Education, Inc., Los Angeles, Calif., USA 1993, 153–157, and Deghenghi et al., *Life Sci.* 1994, 54, 1321–1328):

```
GHRP-1      Ala-His-D-(2')-Nal-Ala-Trp-D-Phe-Lys-NH2

GHRP-2      D-Ala-D-(2')-Nal-Ala-Trp-D-Nal-Lys-NH2

Hexarelin   His-D-2-MeTrp-Ala-Trp-D-Phe-Lys-NH2.
```

GHRP-1, GHRP-2, GHRP-6, and hexarelin are synthetic growth-hormone secretagogues. Growth-hormone secretagogues stimulate secretion of growth hormone by a mechanism different from that of growth hormone-releasing hormone, but like growth hormone-releasing hormone, they antagonize release of somatostatin from the pituitary and hypothalamus. (Bowers et al., *Endocrinology* 1984, 114, 1537–1545, Cheng et al., *Endocrinology* 1989, 124, 2791–2798, Bowers, C. Y. Novel GH-Releasing Peptides. In: *Molecular and Clinical Advances in Pituitary Disorders*. Ed: Melmed, S.; Endocrine Research and Education, Inc., Los Angeles, Calif., USA 1993, 153–157, and Deghenghi et al., *Life Sci.* 1994, 54, 1321–1328.)

The low oral bioavailability (<1%) of the peptidyl growth-hormone secretagogues stimulated search for non-peptide compounds mimicking action of GHRP-6 in the pituitary. Several benzolactams and spiroindanes have been reported to stimulate growth-hormone release in various animal species and in man. (Smith et al., *Science* 1993, 260, 1640–1643, Patchett et al., *Proc. Natl. Acad. Sci. USA*. 1995, 92, 7001–7005, and Chen et al., *Bioorg. Med. Chem. Lett.* 1996, 6, 2163–2169.) A specific example of a small spiroindane is MK-0677 (Patchett et al. *Proc. Natl. Acad. Sci. USA*. 1995, 92, 7001–7005):

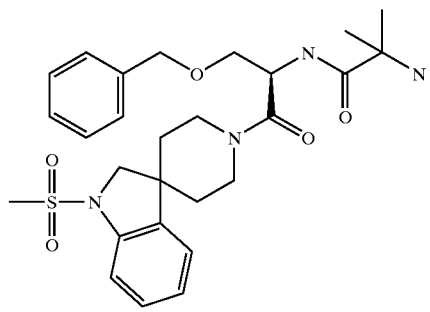

The actions of the above-mentioned growth-hormone secretagogues (both peptide and non-peptide) appear to be mediated by a specific growth-hormone secretagogue receptor (GHS receptor). (Howard et al., *Science* 1996, 273, 974–977, and Pong et al., *Molecular Endocrinology* 1996, 10, 57–61.) This receptor is present in the pituitary and hypothalamus of various mammalian species (GHSR1a) and is distinct from the growth hormone-releasing hormone receptor. The GHS receptor was also detected in the other areas of the central nervous system and in peripheral tissues, for instance adrenal and thyroid glands, heart, lung, kidney and skeletal muscles. (Chen et al., *Bioorg. Med. Chem. Lett.* 1996, 6, 2163–2169, Howard et al., *Science* 1996, 273, 974–977, Pong et al., *Molecular Endocrinology* 1996, 10, 57–61, Guan et al., *Mol. Brain Res.* 1997, 48, 23–29, and McKee et al., *Genomics* 1997, 46, 426–434.) A truncated version of GHSR1a has been reported. (Howard et al., *Science* 1996, 273, 974–977.)

The GHS receptor is a G-protein coupled-receptor. Effects of GHS receptor activation includes depolarization and inhibition of potassium channels, an increase in intercellular concentrations of inositol triphosphate (IP3), and a transient increase in the concentrations of intracellular calcium. (Pong et al., *Molecular Endocrinology* 1996, 10, 57–61, Guan et al., *Mol. Brain Res.* 1997, 48, 23–29, and McKee et al., *Genomics* 1997, 46, 426–434.)

SUMMARY OF THE INVENTION

The present invention features truncated ghrelin analogs active at the GHS receptor. Ghrelin is a naturally occurring modified peptide. The analogs can bind to the GHS receptor and, preferably, bring about signal transduction. Ghrelin analogs have a variety of different uses including being used as a research tool and being used therapeutically.

The structure of human ghrelin is as follows (where the chemical structure of a modified serine is shown, and unmodified amino acids are noted using one letter codes):

(SEQ.ID.NO.1)

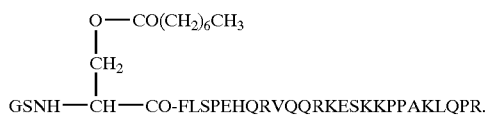

A core region present in ghrelin was found to provide for activity at the GHS receptor. The core region comprises the four N-terminal amino acids, where the serine at position 2 or 3 is modified with a bulky hydrophobic R group.

Thus, a first aspect of the present invention describes a truncated ghrelin analog having a structure selected from the group consisting of:

a) $Z^1$-GSXF(Z)$_n$—$Z^2$; and b) $Z^1$-GXSF(Z)$_n$—$Z^2$;

wherein X is a modified amino acid containing a bulky hydrophobic R group;

each Z is independently either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$Z^1$ is an optionally present protecting group that, if present, is covalently joined to the N-terminal amino group;

$Z^2$ is an optionally present protecting group that, if present, is covalently joined to the C-terminal carboxy group; and n is 0 to 19;

or a pharmaceutically acceptable salt thereof.

Unless otherwise stated, those amino acids with a chiral center are provided in the L-enantiomer. Reference to "a derivative thereof" refers to a modified amino acid such as the corresponding D-amino acid, a N-alkyl-amino acid, a β-amino acid, or a labeled amino acid.

Another aspect of the present invention describes a method of screening for a compound able to bind to a GHS receptor. The method comprises the step of measuring the ability of a compound to affect binding of a truncated ghrelin analog to either the receptor, a fragment of the receptor comprising a ghrelin binding site, a polypeptide comprising the fragment, or a derivative of the polypeptide.

Another aspect of the present invention describes a method for achieving a beneficial affect in a subject comprising the step of administering to the subject an effective amount of a ghrelin analog. The effective amount produces a beneficial effect in helping to treat (e.g., cure or reduce the severity) or prevent (e.g., reduce the likelihood of onset or severity) a disease or disorder.

Another aspect of the present invention describes a method for stimulating growth hormone secretion comprising the step of administering to a subject an effective amount of a ghrelin analog. The effective amount is at least an amount sufficient to produce a detectable increase in growth hormone secretion and, preferably, is an amount sufficient to achieve a beneficial affect in a patient.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present invention features truncated ghrelin analogs active at the GHS receptor. Human ghrelin is a 28 amino acid modified peptide where a serine hydroxyl group is esterified by n-octanoic acid. (Kojima et al., *Nature* 1999, 402, 656–660, and Kojima, (Abstract), Third International Symposium on Growth Hormone Secretagogues, Keystone, Colo., USA Feb. 17–19, 2000.)

Ghrelin induces growth hormone release from primary-culture pituitary cells in a dose-dependent manner without stimulating the release of the other pituitary hormones. Injected intravenously into anaesthetized rats, ghrelin stimulated pulsatile release of growth hormone. (Kojima et al., *Nature* 1999, 402, 656–660.)

Truncated ghrelin analogs described herein are active at the GHS receptor. The analogs can bind to the receptor, and preferably, stimulate receptor activity. Ghrelin analogs have a variety of different uses including being used as a research tool and being used therapeutically.

Research tool applications generally involve the use of a truncated ghrelin analog and the presence of a GHS receptor or fragment thereof. The GHS receptor can be present in different environments such as a mammalian subject, a whole cell, or membrane fragments. Examples of research tool applications include screening for compounds active at the GHS receptor, determining the presence of the GHS receptor in a sample or preparation, and examining the role or effect of ghrelin.

Ghrelin analogs can be used to screen for both ghrelin agonists and ghrelin antagonists. Screening for ghrelin agonists can be performed, for example, by using a ghrelin analog in a competition experiment with test compounds. Screening for ghrelin antagonists can be performed, for example, by using a ghrelin analog to produce GHS receptor activity and then measuring the ability of a compound to alter GHS receptor activity.

Ghrelin analogs can be administered to a subject. A "subject" refers to a mammal including, for example, a human, a rat, a mouse, or a farm animal. Reference to subject does not necessarily indicate the presence of a disease or disorder. The term subject includes, for example, mammals being dosed with a truncated ghrelin analog as part of an experiment, mammals being treated to help alleviate a disease or disorder, and mammals being treated prophylactically to retard or prevent the onset of a disease or disorder.

Ghrelin agonists can be used to achieve a beneficial effect in a subject such as one or more of the following: treating a growth hormone deficient state, increasing muscle mass, increasing bone density, treating sexual dysfunction in males or females, facilitating a weight gain, facilitating maintenance of weight, facilitating maintenance of physical functioning, facilitating recovery of physical function, and/or facilitating appetite increase. Facilitating a weight gain, maintenance in weight, or appetite increase is particularly useful for a patient having a disease or disorder, or under going a treatment, accompanied by weight loss. Examples of diseases or disorders accompanied by weight loss include anorexia, bulimia, cancer cachexia, AIDS, wasting, cachexia, and wasting in frail elderly. Examples of treatments accompanied by weight loss include chemotherapy, radiation therapy, temporary or permanent immobilization, and dialysis.

Ghrelin antagonists can also be used to achieve a beneficial effect in a patient. For example, a ghrelin antagonist can be used to facilitate weight loss, facilitate appetite decrease, facilitate weight maintenance, treat obesity, treat diabetes, treat complications of diabetes including retinopathy, and/or treat cardiovascular disorders. Excessive weight is a contributing factor to different diseases including hypertension, diabetes, dyslipidemias, cardiovascular disease, gall stones, osteoarthritis and certain forms of cancers. Bringing about a weight loss can be used, for example, to reduce the likelihood of such diseases and as part of a treatment for such diseases.

Truncated Ghrelin Analogs

The smaller size of truncated ghrelin analogs offers advantages over longer-length ghrelin such as ease of synthesis and/or increased solubility in physiological buffers. In addition, small analogs can serve as models for producing peptidomimetics having desirable pharmacological properties.

Truncated ghrelin analogs described herein have the structure:

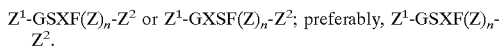

wherein X is a modified amino acid containing a bulky hydrophobic R group;

each Z is independently either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$Z^1$ is an optionally present protecting group that, if present, is covalently joined to the N-terminal amino group;

$Z^2$ is an optionally present protecting group that, if present, is covalently joined to the C-terminal carboxy group; and n is 0 to 19; in different embodiments n is 0–3, 0–6, 0–11, 0, 1, 2, 3, 4, 5, 6, 7, 8, 9, 10, or11;

or a pharmaceutically acceptable salt thereof.

Individual amino acids such as those present in the general structure of a truncated ghrelin analog or a $(Z)_n$ group can be represented as follows: A=Ala=Alanine; C=Cys=Cysteine; D=Asp=Aspartic acid; E=Glu=Glutamic acid; F=Phe=Phenylalanine; G=Gly=Glycine; H=His= Histidine; I=Ile=Isoleucine; K=Lys=Lysine; L=Leu= Leucine; M=Met=Methionine; N=Asn=Asparagine; P=Pro= Proline; Q=Gln=Glutamine; R=Arg=Arginine; S=Ser= Serine; T=Thr=Threonine; V=Val=Valine; W=Trp= Tryptophan; and Y=Tyr=Tyrosine.

The present invention includes diastereomers as well as their racemic and resolved enantiomerically pure forms. Truncated ghrelin analogs can contain D-amino acids, L-amino acids or a combination thereof. Preferably, amino acids present in a truncated ghrelin analog are the L-enantiomer.

Since each Z is independently selected, the resulting $(Z)_n$ group is not limited to a group of contiguous amino acids present in ghrelin. In an embodiment of the present invention $(Z)_n$ is a contiguous amino acid group present in ghrelin.

The design of analogs where $(Z)_n$ is a contiguous amino acid group not present in ghrelin can be based on substitutions to ghrelin, or a truncated ghrelin, where the substitutions take into account differences in amino acids R groups. An R group affects different properties of the amino acid such as physical size, charge, and hydrophobicity. Amino acids can be divided into different groups as follows: neutral and hydrophobic (alanine, valine, leucine, isoleucine, proline, tryptophan, phenylalaine, and methionine); neutral and polar (glycine, serine, threonine, tyrosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in peptide functioning.

Preferred derivatives are D-amino acids, N-allyl-amino acids, β-amino acids, or a labeled amino acid (including a labeled version of a D-amino acid, a N-alkyl-amino acids, or a β-amino acid). A labeled derivative indicates the alteration of an amino acid or amino acid derivative with a detectable label. Examples of detectable labels include luminescent, enzymatic, and radioactive labels. Both the type of label and the position of the label can effect analog activity. Labels should be selected and positioned so as not to substantially alter the activity of the truncated ghrelin analog at the GHS receptor. The effect of a particular label and position on ghrelin activity can be determined using assays measuring ghrelin activity and/or binding.

A protecting group covalently joined to the N-terminal amino group reduces the reactivity of the amino terminus under in vivo conditions. Amino protecting groups include —$C_{1-10}$ alkyl, —$C_{1-10}$ substituted alkyl, —$C_{2-10}$ alkenyl, —$C_{2-10}$ substituted alkenyl, aryl, —$C_{1-6}$ alkyl aryl, —C(O)—$(CH_2)_{1-6}$—COOH, —C(O)—$C_{1-6}$ alkyl, —C(O)-aryl, —C(O)—O—$C_{1-6}$ alkyl, or —C(O)—O-aryl. Preferably, the amino terminus protecting group is acetyl, propyl, succinyl, benzyl, benzyloxycarbonyl or t-butyloxycarbonyl.

A protecting group covalently joined to the C-terminal carboxy group reduces the reactivity of the carboxy terminus under in vivo conditions. The carboxy terminus protecting group is preferably attached to the α-carbonyl group of the last amino acid. Carboxy terminus protecting groups include amide, methylamide, and ethylamide.

In a preferred embodiment X has the structure:

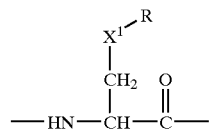

wherein $X^1$ is either —O—, —S—, —OC(O)—, —NHC (O)—, or —$CH_2$—; preferably, $X^1$ is either —OC(O)— or —NHC(O)—, more preferably, $X^1$ is —OC(O)—; and R is either a longer length alkyl, substituted longer length alkyl, longer length alkenyl, substituted longer length alkenyl, longer length heteroalkyl, substituted longer length heteroalkyl, aryl, or alkylaryl; preferably, R is either —$C_{4-20}$ alkyl, —$C_{4-20}$ substituted alkyl, —$C_{4-20}$ substituted alkenyl, —$C_{4-20}$ alkenyl, —$C_{4-20}$ heteroalkyl, —$C_{4-20}$ substituted heteroalkyl, aryl, or alkylaryl; more preferably, R is a —$C_{5-15}$ alkyl or a —$C_{5-15}$ substituted alkyl; more preferably R is a —$C_{5-15}$; more preferably, R is —$(CH_2)_6CH_3$.

Examples of truncated ghrelin analogs including the following modified peptides:
GSXFLSPEHQRVQQ (compound 13, SEQ. ID. NO. 2),
GSX$^b$FLSPEHQRVQQ (compound 14, SEQ. ID. NO. 3),
GSXFLSPEHQRVQQRKESKKPPA-NH$_2$ (compound 18, SEQ. ID. NO. 4),
GSXFLSPEHQRVQQRKES-NH$_2$ (compound 19, SEQ. ID. NO. 5),
GSXFLSPEHQ-NH$_2$ (compound 20, SEQ. ID. NO. 6),
GSXFL-NH$_2$ (compound 21),
GSXF-NH$_2$ (compound 22),
wherein X is

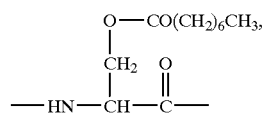

and $X^b$ is

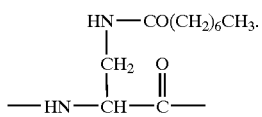

The effect of particular groups, such as X, $(Z)_n$ or blocking groups on ghrelin analog activity at the GHS receptor can be determined using techniques such as those described in the examples provided below. In different embodiments a truncated ghrelin analog has at least about 50%, at least about 60%, at least about 70%, at least about 80%, or at least about 90%, functional activity relative to ghrelin as determined using the assay described in the Example 3 infra; and/or has an $IC_{50}$ greater than about 1,000, greater than about 100, or greater than about 50 using the binding assay described in Example 2 infra. With respect to $IC_{50}$, greater refers to potency and thus indicates a lesser amount is needed to achieve binding inhibition.

Truncated ghrelin analogs can be produced using techniques well known in the art. For example, a polypeptide region of a truncated ghrelin analog can be chemically or biochemically synthesized and modified. Techniques for chemical synthesis of polypeptides are well known in the art. (See e.g., Vincent in *Peptide and Protein Drug Delivery*, New York, N.Y., Dekker, 1990.) Examples of techniques for biochemical synthesis involving the introduction of a nucleic acid into a cell and expression of nucleic acids are provided in Ausubel, *Current Protocols in Molecular Biology*, John Wiley, 1987–1998, and Sambrook et al., in *Molecular Cloning, A Laboratory Manual*, $2^{nd}$ Edition, Cold Spring Harbor Laboratory Press, 1989.

Chemical Definitions

Definitions of some of the chemical groups making up a protecting group or present in an R group are provided below.

"Alkyl" refers to a hydrocarbon group containing one or more carbon atoms, where multiple carbon atoms if present are joined by single bonds. The alkyl hydrocarbon group may be straight-chain or contain one or more branches or cyclic groups. Protecting group hydrocarbons are preferably $C_{1-4}$. R alkyl groups are preferably about 4 to about 20 carbon atoms in length, more preferably $C_{5-15}$, and more preferably —$(CH_2)_6CH_3$. Reference to "longer length alkyl" indicates at least about 4 carbon atoms.

"Substituted alkyl" refers to an alkyl wherein one or more hydrogens of the hydrocarbon group are replaced with one or more substituents selected from the group consisting of halogen (preferably —F or —Cl), —OH, —CN, —SH, —$NH_2$, —$NHCH_3$, —$NO_2$, —$C_{1-2}$ alkyl substituted with 1 to 6 halogens (preferably —F or —Cl, more preferably —F), —$CF_3$, —$OCH_3$, —$OCF_3$, and —$(CH_2)_{0-4}$—COOH. In different embodiments 1, 2, 3 or 4 substituents are present. The presence of —$(CH_2)_{0-4}$—COOH results in the production of an alkyl acid. Examples of alkyl acids containing, or consisting of, —$(CH_2)_{0-4}$—COOH include 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following groups: amino, amido, —O—, or carbonyl. In different embodiments 1 or 2 heteroatoms are present.

"Substituted hetereoalkyl" refers to a heteroalkyl wherein one or more hydrogens of the hydrocarbon group are replaced with one or more substituents selected from the group consisting of halogen (preferably —F or —Cl), —OH, —CN, —SH, —$NH_2$, —$NHCH_3$, —$NO_2$, —$C_{1-2}$ alkyl substituted with 1 to 6 halogens (preferably —F or —Cl, more preferably —F), —$CF_3$, —$OCH_3$, —$OCF_3$, and —$(CH_2)_{0-4}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups. Protecting group hydrocarbons are preferably $C_{2-4}$. R alkenyl groups are preferably about 4 to about 20 carbon atoms in length, more preferably $C_{5-15}$. Reference to "longer length alkenyl" indicates at least about 4 carbon atoms.

"Substituted alkenyl" refers to an alkenyl wherein one or more hydrogens are replaced with one or more substituents selected from the group consisting of halogen (preferably —F or —Cl), —OH, —CN, —SH, —$NH_2$, —$NHCH_3$, —$NO_2$, —$C_{1-2}$ alkyl substituted with 1 to 6 halogens (preferably —F or —Cl, more preferably —F), —$CF_3$, —$OCH_3$, —$OCF_3$, and —$(CH_2)_{0-4}$—COOH. In different embodiments 1, 2, 3 or 4 substituents are present.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-antracene. Aryl substituents are selected from the group consisting of —$C_{1-4}$ alkyl, —$C_{1-4}$ alkoxy, halogen (preferably —F or —Cl), —OH, —CN, —SH, —$NH_2$, —$NO_2$, —$C_{1-2}$ alkyl substituted with 1 to 5 halogens (preferably —F or —Cl, more preferably —F), —$CF_3$, —$OCF_3$, and —$(CH_2)_{0-4}$—COOH. In different embodiments the aryl contains 0, 1, 2, 3, or 4 substituents.

"Alkylaryl" refers to an "alkyl" joined to an "aryl".

GHS Receptor Binding Assay

Assays measuring the ability of a compound to bind a GHS receptor employ a GHS receptor, a fragment of the receptor comprising a ghrelin binding site, a polypeptide comprising such a fragment, or a derivative of the polypeptide. Preferably, the assay uses the GHS receptor or a fragment thereof.

A polypeptide comprising a GHS receptor fragment that binds ghrelin can also contain one or more polypeptide regions not found in a GHS receptor. A derivative of such a polypeptide comprises a GHS receptor fragment that binds ghrelin along with one or more non-peptide components.

The GHS receptor amino acid sequence involved in ghrelin binding can be readily identified using labeled ghrelin or truncated ghrelin analogs and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding ghrelin can be subdivided to further locate the ghrelin binding region. Fragments used for binding studies can be generated using recombinant nucleic acid techniques.

Binding assays can be performed using individual compounds or preparations containing different numbers of compounds. A preparation containing different numbers of compounds having the ability to bind to the GHS receptor can be divided into smaller groups of compounds that can be tested to identify the compound(s) binding to the GHS receptor. In an embodiment of the present invention, a test preparation containing at least 10 compounds is used in a binding assay.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

Screening for GHS Receptor Active Compounds

Screening for GHS receptor active compounds is facilitated using a recombinantly expressed receptor. Using a recombinantly expressed GHS receptor offers several advantages such as the ability to express the receptor in a defined cell system so that a response to a compound at the GHS receptor can more readily be differentiated from responses at other receptors. For example, the GHS receptor can be expressed in a cell line such as HEK 293, COS 7, and CHO not normally expressing the receptor by an expression vector, wherein the same cell line without the expression vector can act as a control.

Screening for compounds reducing GHS receptor activity is facilitated through the use of a truncated ghrelin analog in the assay. The use of a truncated ghrelin analog in a screening assay provides for GHS receptor activity. The effect of test compounds on such activity can be measured to identify, for example, allosteric modulators and antagonists.

GHS receptor activity can be measured using different techniques such as detecting a change in the intracellular conformation of the GHS receptor, in the G-protein coupled activities, and/or in the intracellular messengers. Preferably, GHS receptor activity is measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button et al., 1993, *Cell Calcium* 14, 663–671, and Feighner et al., 1999, *Science* 284, 2184–2188.)

Chimeric receptors containing a ghrelin binding region functionally coupled to a different G-protein can also be used to measure GHS receptor activity. A chimeric GHS receptor contains an N-terminal extracellular domain; a transmembrane domain made up of transmembrane regions, extracellular loop regions, and intracellular loop regions; and an intracellular carboxy terminus. Techniques for producing chimeric receptors and measuring G-protein coupled responses are provided in, for example, International Application Number WO 97/05252, and U.S. Pat. No. 5,264,565, both of which are hereby incorporated by reference herein.

Stimulation of GHS Receptor Activity

Truncated ghrelin analogs can be used to stimulate GHS receptor activity. Such stimulation can be used, for example, to study the effect of GHS receptor modulation, to study the effect of growth hormone secretion, to look for or study ghrelin antagonists, or to achieve a beneficial effect in a subject. Beneficial effects that can be achieved include one or more of the following: treating a growth hormone deficient state, increasing muscle mass, increasing bone density, treating sexual dysfunction in males or females, facilitating a weight gain, facilitating maintenance of weight, facilitating maintenance of physical functioning, facilitating recovery of physical function, and/or facilitating appetite increase.

Increasing weight or appetite can be useful for maintaining weight or producing a weight or appetite gain in an under weight subject, or in a patient having a disease or undergoing treatment that affects weight or appetite. In addition, for example, farm animals such as pigs, cows and chickens can be treated to gain weight.

Under weight subjects include those having a body weight about 10% or less, 20% or less, or 30% or less, than the lower end of a "normal" weight range or Body Mass Index ("BMI"). "Normal" weight ranges are well known in the art and take into account factors such as a patient age, height, and body type.

BMI measures your height/weight ratio. It is determined by calculating weight in kilograms divided by the square of height in meters. The BMI "normal" range is 19–22.

Administration

Truncated ghrelin analogs can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18$^{th}$ *Edition*, Ed. Gennaro, Mack Publishing, 1990, and *Modern Pharmaceutics* 2$^{nd}$ *Edition*, Eds. Banker and Rhodes, Marcel Dekker, Inc., 1990, both of which are hereby incorporated by reference herein.

Truncated ghrelin analogs can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Truncated ghrelin analogs can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

Truncated ghrelin analogs may also be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Truncated ghrelin analogs can be provided in kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable affect and the amount of dosage form to be taken over a specified time period.

EXAMPLES

Examples are provided below to further illustrate different features of the present invention. The examples also illustrate useful methodology for practicing the invention. These examples do not limit the claimed invention.

Example 1

Peptide Synthesis Purification and Characterization

Fmoc-protected amino acids were obtained from AnaSpec (San Jose, Calif.), 4-(2',4'-dimethoxyphenyl-Fmoc-aminomethyl)-phenoxy resin from PE Biosystems (Foster City, Calif.), Boc-7-aminoheptanoic acid from Bachem (King of Prussia, Pa.) and n-octanoic acid, 2,4,6-octatrienoic acid, 2-propylpentanoic acid, 11-undecanoic acid, palmitic acid, 8-bromooctanoic acid, 1-adamanteneacetic acid and benzoic acid from Aldrich (Milwaukee, Wis.).

Elongation of peptidyl chains on 4-(2',4'-dimethoxyphenyl-Fmoc-aminomethyl)-phenoxy resin was performed on a 431A ABI peptide synthesizer. Manufacture-supplied protocols were applied for coupling of the hydroxybenzotriazole esters of amino acids in N-methylpyrrolidone (NMP). The fluorenylmethyloxycarbonyl (Fmoc) group was used as a semipermanent α-amino protecting group, whereas the side chains protecting groups were: tert-butyl for serine, trityl for serine in position 3 and for histidine and glutamine, tert-butyl ester for glutamic acid, 2,2,4,6,7,-pentamethyldihydrobenzofuran-5-sulfonyl (Pbf) for arginine, tert-buthyloxycarbonyl (Boc) for lysine and for α-amino group of glycine in position 1.

The peptidyl resin was then transferred into a vessel and the trityl group from the side chain of Ser$^3$ was manually removed with 1% trifluoroacetic acid (TFA) in dichloromethane (45 minutes at room temperature). The peptidyl resin was thoroughly washed, and then agitated for 4 hours with the 6-fold excess of each 1-ethyl-3-(3-dimethyl-aminopropyl)carbodiimide (EDC) and a selected acid in DCM or NMP, in the presence of a catalytic amount of 4-dimethylaminopyridine (ca. 10 mg). The peptidyl resin was again washed with DCM, NMP and methanol, dried and treated with TFA in the presence of scavengers (ca. 3% total of the mixture of water-anisole-triethylsilane, 1:1:1, v/v/v). After 1.5 hours, the resin was filtered off, TFA was removed in vacuo and the residue was triturated with ether. The precipitate which formed was filtered off, washed thoroughly with ether and dried.

The crude peptide was analyzed by analytical reverse-phase high-pressure liquid chromatography (RP HPLC) on a C18 Vydac column attached to a Waters 600E system with automatic Wisp 712 injector and 991 Photodiode Array detector. A standard gradient system of 0–100% buffer B in 30 minutes (G1), or a gradient of 20–80% buffer B in 30 minutes (G2), was used for analysis; buffer A was 0.1% trifluoroacetic acid in water and buffer B was 0.1% trifluoroacetic acid in acetonitrile. HPLC profiles were recorded at 210 nm and 230 nm.

Preparative separations were performed on a Waters Delta Prep 4000 system with a semipreparative C18 RP Vydac column. The above-described solvent system of water and acetonitrile, in a gradient of 20–80% buffer B in 60 minutes (G3) or in a gradient of 0–60% buffer B, was used for separations.

The chromatographically homogenous compounds were analyzed by electrospray mass spectrometry (Hewlett Packard Series 1100 MSD spectrometer).

Example 2

Binding Assay

Binding of [$^{35}$S]-MK-677 to crude membranes prepared from HEK 293-aequorin stable cell lines was performed as described in Chen et al., Bioorg. Med. Chem. Lett. 1996, 6, 2163–2169, and Howard et al., Science 1996, 273, 974–977. Prior to the binding assay, the HEK 293-AEQ17 cells ($8 \times 10^5$ cells plated 18 hours before transfection in a T75 flask) were transfected with 22 μg of human GHS receptor plasmid using 264 μg lipofectamine. The open reading frame cDNA (SEQ. ID. NO. 22) encoding the human GHS receptor inserted in the mammalian expression vector pcDNA-3 (Invitrogen, Carlsbad, Calif.) was used for binding and expression studies.

For a 96-well filter binding assay, 0.05 nM [$^{35}$S]-NM-677 (specific activity ~1200 Ci/mmol) was bound to 4 μg membrane protein per well with or without competing test ligand. The bound membranes were filtered on 0.5% polyethylenimine prewet filters (UniFilter 96 GF/C; Packard #6005174, Meriden, Conn.). Filters were washed 8 times, dried, and counted with Microscint 20 (Packard #6013621, Meriden, Conn.). IC$_{50}$ values were determined from three separate assays performed in triplicate. SEQ. ID. NO. 22 is as follows:

ATGTGGAACGCGACGCCCAGCGAAGAGCCGGGGTTCAACCTCACACTGGC

CGACCTGGACTGGGATGCTTCCCCCGGCAACGACTCGCTGGGCGACGAGC

TGCTGCAGCTCTTCCCCGCGCCGCTGCTGGCGGGCGTCACAGCCACCTGC

GTGGCACTCTTCGTGGTGGGTATCGCTGGCAACCTGCTCACCATGCTGGT

GGTGTCGCGCTTCCGCGAGCTGCGCACCACCACCAACCTCTACCTGTCCA

GCATGGCCTTCTCCGATCTGCTCATCTTCCTCTGCATGCCCCTGGACCTC

GTTCGCCTCTGGCAGTACCGGCCCTGGAACTTCGGCGACCTCCTCTGCAA

ACTCTTCCAATTCGTCAGTGAGAGCTGCACCTACGCCACGGTGCTCACCA

TCACAGCGCTGAGCGTCGAGCGCTACTTCGCCATCTGCTTCCCACTCCGG

GCCAAGGTGGTGGTCACCAAGGGGCGGGTGAAGCTGGTCATCTTCGTCAT

CTGGGCCGTGGCCTTCTGCAGCGCCGGGCCCATCTTCGTGCTAGTCGGGG

TGGAGCACGAGAACGGCACCGACCCTTGGGACACCAACGAGTGCCGCCCC

ACCGAGTTTGCGGTGCGCTCTGGACTGCTCACGGTCATGGTGTGGGTGTC

CAGCATCTTCTTCTTCCTTCCTGTCTTCTGTCTCACGGTCCTCTACAGTC

TCATCGGCAGGAAGCTGTGGCGGAGGAGGCGCGGCGATGCTGTCGTGGGT

GCCTCGCTCAGGGACCAGAACCACAAGCAAACCGTGAAAATGCTGGCTGT

AGTGGTGTTTGCCTTCATCCTCTGCTGGCTCCCCTTCCACGTAGGGCGAT

ATTTATTTTCCAAATCCTTTGAGCCTGGCTCCTTGGAGATTGCTCAGATC

AGCCAGTACTGCAACCTCGTGTCCTTTGTCCTCTTCTACCTCAGTGCTGC

CATCAACCCCATTCTGTACAACATCATGTCCAAGAAGTACCGGGTGGCAG

TGTTCAGACTTCTGGGATTCGAACCCTTCTCCCAGAGAAAGCTCTCCACT

CTGAAAGATGAAAGTTCTCGGGCCTGGACAGAATCTAGTATTAATACATG

A

Example 3

Aequorin Bioluminescence Functional Assay

The aequorin bioluminescence assay is a reliable test for identifying G-protein coupled receptors which couple through the Gα protein subunit family consisting of Gq and G11. Coupling through Gq and G11 leads to the activation of phospholipase C, mobilization of intracellular calcium and activation of protein kinase C. A stable cell line expressing the human GHSR1a and the aequorin reporter protein were used for the assay. (Button et al., *Cell Calcium* 1993, 14, 663–671.)

The assay was performed using a Luminoskan RT luminometer (Labsystems Inc., Gaithersburg, Md.) controlled by custom software written for a Macintosh PowerPC 6100. 293AEQ17/GHSR1a cells (as described in Example 2), were cultured for 72 hours and the apo-aequorin in the cells was charged for 1 hour with coelenterazine (10 $\mu$M) under reducing conditions (300 $\mu$M reduced glutathione) in ECB buffer (140 mM NaCl, 20 mM KCl, 20 mM HEPES-NaOH [pH=7.4], 5 mM glucose, 1 mM MgCl$_2$, 1 mM CaCl$_2$, 0.1 mg/ml bovine serum albumin). The cells were harvested, washed once in ECB medium and resuspended to 500,000 cells/ml. 100 ml of cell suspension (corresponding to 5×10$^4$ cells) was then injected into the test plate containing the peptides, and the integrated light emission was recorded over 30 seconds, in 0.5 second units. 20 $\mu$L of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton X-100 lysis response. The functional EC$_{50}$ values were measured in three separate assays.

Example 4

Activity of Different Types of Ghlerin Analogs

Analogs of human ghrelin (Tables 1–4) were prepared by solid phase syntheses as described in Example 1. The analogs were evaluated for their binding affinities to the cloned human GHS receptor 1a in a competitive binding assay with [$^{35}$S]-MK-677 as the radiolabeled ligand, and also for their ability to stimulate inositol triphosphate-coupled mobilization of intracellular calcium in HEK-293 cells expressing hGHSR1a, as described in Examples 2 and 3.

The role of the n-octanoyl group in interaction of human ghrelin with hGHSR1a was examined by testing compounds in which the hydroxyl group in the side chain of Ser$^3$ was acylated by various aliphatic or aromatic acids (see Table 1). Acylation of Ser$^3$ with hydrophobic acids resembling in size n-octanoic acid, such as the unsaturated 2,4,6-octatrienoic acid or the branched 2-propylpentanoic acid, or the longer chain 11-undecanoic acid. or palmitic acid, yielded compounds 1–4 having agonist potencies similar to that of ghrelin. In contrast, replacement of the n-octanoyl group with the substantially smaller acetyl group led to compound 5 which was 20-fold less potent than human ghrelin in the hGHSR1a activation assay. Ghrelin without the n-octanoyl group (des-octanoyl-ghrelin) poorly activated hGHSR1a even at micromolar concentrations (compound 6 in Table 1).

To explore possible non-hydrophobic interactions with the receptor, the hydroxyl group of serine 3 in compounds 7, 8, 9 was acylated with aliphatic acids which mimic the extended hydrophobic chain of n-octanoic acid, but also contain bromo, amino or amido groups. In the hGHSR1a activation assay, analogs with amido and amino groups in the side chain of residue 3 were respectively 5- and 20-fold less potent as agonists at hGHSR1a (compounds 8 and 9 in Table 1), whereas, compound 7 with 8-bromooctanoyl group attached to the side chain of Ser$^3$ retained the potency of the parent compound. Compound 10 having the bulky and rigid hydrophobic 1-adamantaneacetyl group in place of n-octanoyl group in position 3 activated hGHSR1a as efficiently as ghrelin, while compound 11 having a smaller benzoyl group in the same position was 2-fold less potent.

Table 2 illustrates the effect of attaching the n-octanoyl group to the side chain of residue 3 through an amide bond. In compounds 12 and 14, 2,3-di-amino-propionic acid was incorporated in place of Ser$^3$ and the β-amino group of this new residue was acylated with n-octanoic acid. Compounds of 12 and 14 activated hGHSR1a as efficiently as the parent compounds, ghrelin and the compound 13 (peptide encompassing 1 to 14 residues of ghrelin).

Table 3 provides binding and functional data on ghrelin analogs with the hydroxyl groups of serine residues other then Ser$^3$ esterified by n-octanoic acid. Compound 15 with modified Ser$^2$, was active. Compounds 16 and 17, with modified Ser$^6$ or Ser$^{18}$, were inactive even at micromolar concentrations.

Table 4 provides binding and functional data on truncated analogs. Shortening of ghrelin down to its 4 amino terminus residues yielded active peptides. The relative binding affinities gradually decreased with the extent of the C-terminal deletions. Short peptides encompassing residue 1–3, or 2–5, or 3–5, or 2–4 of ghrelin were poor activators even at micromolar concentrations.

TABLE 1

Analogs of Human Ghrelin Modified at Position 3

| Compound | X | Binding Assay $IC_{50}$ (nM) | Functional Assay $EC_{50}$ (nM) | % activation at 10 μM relative to ghrelin |
|---|---|---|---|---|
| Human Ghrelin | $CO—(CH_2)_6CH_3$ | $0.25 \pm 0.07$ | $32 \pm 4.5$ | 100 |
| 1 | $CO—CH=CH—CH=CH—CH=CH—CH_3$ | $0.98 \pm 0.36$ | $39 \pm 10$ | $108 \pm 1$ |
| 2 | $CO—CH(CH_2CH_2CH_3)_2$ | $0.96 \pm 0.05$ | $38 \pm 11$ | $103 \pm 1$ |
| 3 | $CO—(CH_2)_9CH_3$ | $0.12 \pm 0.03$ | $9.1 \pm 6.2$ | $104 \pm 3$ |
| 4 | $CO—(CH_2)_{14}CH_3$ | $0.87 \pm 0.17$ | $8.3 \pm 0.6$ | $96 \pm 11$ |
| 5 | $CO—CH_3$ | >2000 | $2000 \pm 480$ | $59 \pm 13$ |
| 6 | — | >10,000 | >10,000 | $41 \pm 4$ |
| 7 | $CO—(CH_2)_6CH_2Br$ | $0.08 \pm 0.0$ | $18 \pm 0.9$ | $88 \pm 7$ |
| 8 | $CO—(CH_2)_2CO—NH—(CH_2)_2CH_3$ | $1020 \pm 202$ | $410 \pm 120$ | $86 \pm 10$ |
| 9 | $CO—(CH_2)_6NH_2$ | >2000 | $1200 \pm 370$ | $68 \pm 3$ |
| 10 | CO—CH₂—adamantyl | $0.12 \pm 0.05$ | $24 \pm 9.5$ | $95 \pm 7$ |
| 11 | CO—phenyl | $11 \pm 1.5$ | $53 \pm 3.2$ | $85 \pm 2$ |

The modification shown in Table 1 is with respect to:

```
        X
        |
GSSFLSPEHQRVQQRLESKKPPAKLQPR
1                          28
```

Compounds 1–11 correspond to SEQ. ID. NOs. 7–17.

TABLE 2

Analogs of Human Ghrelin with an Amide Bond in the Side Chain of Residue 3

| Compound | Binding Assay $IC_{50}$ (nM) | Functional Assay $EC_{50}$ (nM) | % activation at 10 μM relative to ghrelin |
|---|---|---|---|
| Human Ghrelin | $0.25 \pm 0.07$ | $32 \pm 4.5$ | 100 |
| 12 | $0.42 \pm 12$ | $31 \pm 9.8$ | $105 \pm 5$ |
| 13 | $9.6 \pm 1.5$ | $17 \pm 4$ | $97 \pm 9$ |
| 14 | $8 \pm 2.7$ | $38 \pm 1.8$ | $102 \pm 3$ |

Compound 12 is a modified amino acid having the following sequence GSX$^b$FLSPEHQRVQQRKESKKPPAKLQPR (SEQ. ID. NO. 18), where X$^b$ is

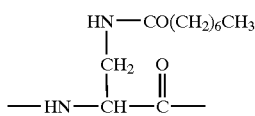

TABLE 3

Analogs of Human Ghrelin Octanoylated at Other Serine Residues

| Compound | Binding Assay $IC_{50}$ (nM) | Functional Assay $EC_{50}$ (nM) | % activation at 10 μM relative to ghrelin |
|---|---|---|---|
| Human Ghrelin | $0.25 \pm 0.07$ | $32 \pm 4.5$ | 100 |
| 15 | $48 \pm 7.2$ | $42 \pm 14$ | $81 \pm 14$ |
| 16 | >1000 | >10,000 | $36 \pm 1$ |
| 17 | >5000 | >10,000 | $46 \pm 2$ |

Compounds 15–17 are as follows:

GXSFLSPEHQRVQQRKESKKPPAKLQPR (compound 15, SEQ. ID. NO. 19),

GSSFLXPEHQRVQQRKESKKPPAKLQPR (compound 16, SEQ. ID. NO. 20),

GSSFLSPEHQRVQQRKEXKKPPAKLQPR (compound 17, SEQ. ID. NO. 21), wherein X is

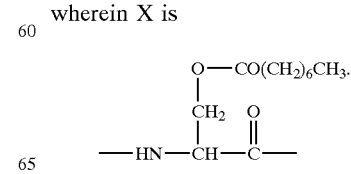

TABLE 4

Truncate Analogs of Human Ghrelin

| Compound | Binding Assay IC$_{50}$ (nM) | Functional Assay | |
|---|---|---|---|
| | | EC$_{50}$ (nM) | % activation at 10 μM relative to ghrelin |
| Human Ghrelin | 0.25 ± 0.07 | 32 ± 4.5 | 100 |
| 18 | 0.16 ± 0.02 | 15 ± 4.5 | 100 ± 4 |
| 19 | 0.77 ± 0.18 | 22 ± 16 | 92 ± 16 |
| 13 | 9.6 ± 1.5 | 17 ± 4 | 97 ± 9 |
| 20 | 7.1 ± 5.7 | 20 ± 6 | 89 ± 17 |
| 21 | 55 ± 10 | 11.5 ± 2.3 | 96 ± 7 |
| 22 | 889 ± 72 | 72 ± 29 | 91 ± 4 |
| 23 | >2000 | 1150 ± 120 | 30 ± 5 |
| 24 | >10,000 | >10,000 | 28 ± 1 |
| 25 | >10,000 | 2500 ± 1200 | 29 ± 7 |
| 26 | >10,000 | >10,000 | 28 ± 1 |

Compounds 23–26 are as follows:

Ac-SXFL-NH$_2$ (compound 23),
GSX-NH$_2$ (compound 24),
Ac-XFL-NH$_2$ (compound 25),
Ac-SXF-NH$_2$ (compound 26),
where X is

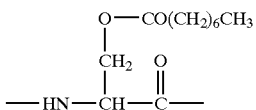

Other embodiments are within the following claims. While several embodiments have been shown and described, various modifications may be made without departing from the spirit and scope of the present invention.

---

What is claimed is:

1. A truncated ghrelin analog consisting of a structure selected from the group consisting of:
   a) $Z^1$-GSXF(Z)$_n$$Z^2$; and
   b) $Z^1$-GXSF(Z)$_n$$Z^2$;
   wherein X is a modified amino acid containing a bulky hydrophobic R group;
   each Z is independently an amino acid selected from the group consisting of alanine, valine, leucine, isoleucine, proline, tryptophan, phenylalanine, methionine, glycine, serine, threonine, tyrosine, cysteine, asparagine, glutamine, lysine, arginine, histidine, aspartic acid, and glutamic acid, or said amino acid labeled with a detectable label selected from the group consisting of a luminescent, enzymatic and radioactive label;
   $Z^1$ is an optionally present protecting group that, if present is covalently joined to the N-terminal amino group;
   $Z^2$ is an optionally present protecting group that, if present is covalently joined to the C-terminal carboxy group; and
   n is 0 to 19;
   or a pharmaceutically accepted salt thereof.

2. The analog of claim 1, wherein X has the structure:

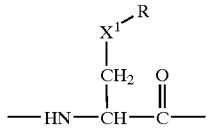

wherein $X^1$ is either —O—, —S—, —OC(O)—, —NHC(O)—, or —CH$_2$—; and
   R is either —C$_{4-20}$ alkyl, —C$_{4-20}$ substituted alkyl, —C$_{4-20}$ substituted alkenyl, —C$_{4-20}$ alkenyl, —C$_{4-20}$ heteroalkyl, —C$_{4-20}$ substituted heteroalkyl, aryl, or alkylaryl.

3. The analog of claim 2, wherein said analog has the structure: $Z^1$-GSXF(Z)$_n$-$Z^2$.

4. The analog of claim 3, wherein n is 0–11.

5. The analog of claim 4, wherein n is 0–6.

6. The analog of claim 5, wherein n is 0–3.

7. The analog of claim 6, wherein n is 0.

8. The analog of claim 4, wherein $X^1$ is —C(O)— or —NH(O)—; and R is a —C$_{5-15}$ alkyl.

9. The analog of claim 8, wherein $X^1$ is —C(O)— and R is —(CH$_2$)$_6$CH$_3$.

10. The analog of claim 9, wherein $Z^1$ if present is —C(O)CH$_3$ and $Z^2$ if present is —NH$_2$.

11. The analog of claim 1, wherein said analog has a modified amino acid sequence selected from the group consisting of:
   GSXFLSPEHQRVQQRKESKKPPA-NH$_2$ (SEQ. ID. NO. 4),
   GSXFLSPEHQRVQQRKES-NH$_2$ (SEQ. ID. NO. 5),
   GSX$^b$FLSPEHQRVQQ (SEQ. ID. NO. 3),
   GSXFLSPEHQ-NH$_2$ (SEQ. ID. NO. 6),
   GSXFL-NH$_2$ and
   GSXF-NH$_2$;
   provided that X is

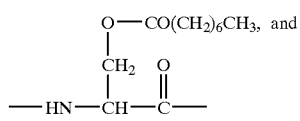

$X^b$ is

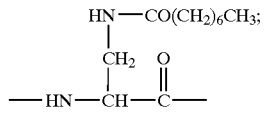

or a pharmaceutically acceptable salt thereof.

12. The analog of claim 11, wherein said analog is GSXFL-NH$_2$, provided that X is

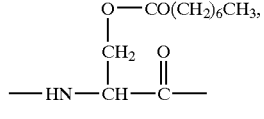

or a pharmaceutically acceptable salt thereof.

13. The analog of claim 11, wherein said analog is GSXF-NH$_2$, provided that X is

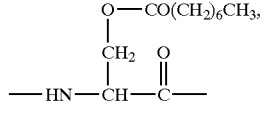

or a pharmaceutically acceptable salt thereof.

14. The analog of claim 1, wherein said analog is GSX-FLSPEHQRVQQ (SEQ ID NO: 2).

* * * * *

SEQUENCE LISTING

<160> NUMBER OF SEQ ID NOS: 22

<210> SEQ ID NO 1
<211> LENGTH: 28
<212> TYPE: PRT
<213> ORGANISM: Human
<220> FEATURE:
<223> OTHER INFORMATION: Xaa = Ser(CO-(CH2)6-CH3)

<400> SEQUENCE: 1

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 2
<211> LENGTH: 14
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-(CH2)6-CH3)

<400> SEQUENCE: 2

Gly Ser Xaa Phe Leu Ser Pro Glu His Gln Arg Val Gln Gln
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Dpr(CO-(CH2)6-CH3)

<400> SEQUENCE: 3

Gly Ser Xaa Phe Leu Ser Pro Glu His Gln Arg Val Gln Gln
 1               5                  10

```
<210> SEQ ID NO 4
<211> LENGTH: 23
<212> TYPE: PRT
<213> ORGANISM: Artificial Sequence
<220> FEATURE:
<223> OTHER INFORMATION: Ghrelin analog
<220> FEATURE:
<221> NAME/KEY: AMIDATION
<222> LOCATION: (23)...(23)
<220> FEATURE:
<221> NAME/KEY: MOD_RES
<222> LOCATION: (3)...(3)
<223> OTHER INFORMATION: Xaa = Ser(CO-(CH2)6-CH3)

<400> SEQUENCE: 4

Gly Ser Xaa Phe Leu Ser Pro Glu His Gln Arg Val Gln Gln Arg Lys
  1               5                  10                  15

Glu Ser Lys Lys Pro Pro Ala
             20

<210> SEQ ID NO 5
<211> LENGTH: 18
<212> TYPE: PRT
<213> ORGANISM: Artificial Sequence
<220> FEATURE:
<223> OTHER INFORMATION: Ghrelin analog
<220> FEATURE:
<221> NAME/KEY: AMIDATION
<222> LOCATION: (18)...(18)
<220> FEATURE:
<221> NAME/KEY: MOD_RES
<222> LOCATION: (3)...(3)
<223> OTHER INFORMATION: Xaa = Ser(CO-(CH2)6-CH3)

<400> SEQUENCE: 5

Gly Ser Xaa Phe Leu Ser Pro Glu His Gln Arg Val Gln Gln Arg Lys
  1               5                  10                  15

Glu Ser

<210> SEQ ID NO 6
<211> LENGTH: 10
<212> TYPE: PRT
<213> ORGANISM: Artificial Sequence
<220> FEATURE:
<223> OTHER INFORMATION: Ghrelin analog
<220> FEATURE:
<221> NAME/KEY: AMIDATION
<222> LOCATION: (10)...(10)
<220> FEATURE:
<221> NAME/KEY: MOD_RES
<222> LOCATION: (3)...(3)
<223> OTHER INFORMATION: Xaa = Ser(CO-(CH2)6-CH3)

<400> SEQUENCE: 6

Gly Ser Xaa Phe Leu Ser Pro Glu His Gln
  1               5                  10

<210> SEQ ID NO 7
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-CH=CH-CH=CH-CH=CH-CH3)
```

```
<400> SEQUENCE: 7

Gly Ser Xaa Phe Leu Ser Pro Glu His Gln Arg Val Gln Gln Arg Lys
 1               5                   10                  15

Glu Ser Lys Lys Pro Pro Ala Lys Leu Gln Pro Arg
            20                  25

<210> SEQ ID NO 8
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-CH(CH2CH2CH3)2)

<400> SEQUENCE: 8

Gly Ser Xaa Phe Leu Ser Pro Glu His Gln Arg Val Gln Gln Arg Lys
 1               5                   10                  15

Glu Ser Lys Lys Pro Pro Ala Lys Leu Gln Pro Arg
            20                  25

<210> SEQ ID NO 9
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-(CH2)9-CH3)

<400> SEQUENCE: 9

Gly Ser Xaa Phe Leu Ser Pro Glu His Gln Arg Val Gln Gln Arg Lys
 1               5                   10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-(CH2)14-CH3)

<400> SEQUENCE: 10

Gly Ser Xaa Phe Leu Ser Pro Glu His Gln Arg Val Gln Gln Arg Lys
 1               5                   10                  15

Glu Ser Lys Lys Pro Pro Ala Lys Leu Gln Pro Arg
            20                  25

<210> SEQ ID NO 11
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-CH3)
```

-continued

```
<400> SEQUENCE: 11

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 12
<211> LENGTH: 28
<212> TYPE: PRT
<213> ORGANISM: Artificial Sequence
<220> FEATURE:
<223> OTHER INFORMATION: Ghrelin analog

<400> SEQUENCE: 12

Gly Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 13
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-(CH2)6-CH2Br)

<400> SEQUENCE: 13

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 14
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-(CH2)2-CO-NH-(CH2)2-CH3)

<400> SEQUENCE: 14

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 15
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-(CH2)6-NH2)
```

```
<400> SEQUENCE: 15

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 16
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(1-adamantaneacetyl)

<400> SEQUENCE: 16

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 17
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Ser(CO-C6H6)

<400> SEQUENCE: 17

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 18
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (3)...(3)
<223> OTHER INFORMATION: Xaa = Dpr(CO-(CH2)6-CH3)

<400> SEQUENCE: 18

Gly Ser Xaa Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 19
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (2)...(2)
<223> OTHER INFORMATION: Xaa = Ser(CO-(CH2)6-CH3)
```

```
<400> SEQUENCE: 19

Gly Xaa Ser Phe Leu Ser Pro Glu His Gln Arg Val Gln Gln Arg Lys
  1               5                  10                  15

Glu Ser Lys Lys Pro Pro Ala Lys Leu Gln Pro Arg
             20                  25

<210> SEQ ID NO 20
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (6)...(6)
<223> OTHER INFORMATION: Xaa = Ser(CO-(CH2)6-CH3)

<400> SEQUENCE: 20

Gly Ser Ser Phe Leu Xaa Pro Glu His Gln Arg Val Gln Gln Arg Lys
  1               5                  10                  15

Glu Ser Lys Lys Pro Pro Ala Lys Leu Gln Pro Arg
             20                  25

<210> SEQ ID NO 21
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MOD_RES
<222> LOCATION: (18)...(18)
<223> OTHER INFORMATION: Xaa = Ser(CO-(CH2)6-CH3)

<400> SEQUENCE: 21

Gly Ser Ser Phe Leu Ser Pro Glu His Gln Arg Val Gln Gln Arg Lys
  1               5                  10                  15

Glu Xaa Lys Lys Pro Pro Ala Lys Leu Gln Pro Arg
             20                  25

<210> SEQ ID NO 22
<211> LENGTH: 1101
<212> TYPE: DNA
<213> ORGANISM: Artificial Sequence
<220> FEATURE:
<223> OTHER INFORMATION: Human GHS receptor cDNA

<400> SEQUENCE: 22
atgtggaacg cgacgcccag cgaagagccg gggttcaacc tcacactggc cgacctggac      60
tgggatgctt cccccggcaa cgactcgctg gcgacgagc tgctgcagct cttccccgcg     120
ccgctgctgg cgggcgtcac agccacctgc gtggcactct cgtggtggg tatcgctggc     180 aacctgctca ccatgctggt ggtgtcgcgc ttccgcgagc tgcgcaccac caccaacctc     240
tacctgtcca gcatggcctt ctccgatctg ctcatcttcc tctgcatgcc cctggacctc     300
gttcgcctct ggcagtaccg gccctggaac ttcggcgacc tcctctgcaa actcttccaa     360
ttcgtcagtg agagctgcac ctacgccacg gtgctcacca tcacagcgct gagcgtcgag     420
cgctacttcg ccatctgctt cccactccgg gccaaggtgg tggtcaccaa ggggcgggtg     480
aagctggtca tcttcgtcat ctgggccgtg gccttctgca gcgccgggcc catcttcgtg     540
ctagtcgggg tggagcacga gaacggcacc gaccccttggg acaccaacga gtgccgcccc     600
accgagtttg cggtgcgctc tggactgctc acggtcatgg tgtgggtgtc cagcatcttc     660
```

```
ttcttccttc ctgtcttctg tctcacggtc ctctacagtc tcatcggcag gaagctgtgg      720
cggaggaggc gcggcgatgc tgtcgtgggt gcctcgctca gggaccagaa ccacaagcaa      780
accgtgaaaa tgctggctgt agtggtgttt gccttcatcc tctgctggct ccccttccac      840
gtagggcgat atttattttc caaatccttt gagcctggct ccttggagat tgctcagatc      900
agccagtact gcaacctcgt gtcctttgtc ctcttctacc tcagtgctgc catcaacccc      960
attctgtaca acatcatgtc caagaagtac cgggtggcag tgttcagact tctgggattc     1020
gaacccttct cccagagaaa gctctccact ctgaaagatg aaagttctcg ggcctggaca     1080
gaatctagta ttaatacatg a                                               1101
```